(12) United States Patent
Schardl et al.

(10) Patent No.: US 6,335,188 B1
(45) Date of Patent: Jan. 1, 2002

(54) ENDOPHYTE ERGOT ALKALOID SYNTHETIC COMPOUNDS, COMPOUNDS WHICH ENCODE THEREFOR AND RELATED METHODS

(75) Inventors: Christopher L. Schardl; Jinghung Wang, both of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/518,657

(22) Filed: Mar. 3, 2000

Related U.S. Application Data

(60) Provisional application No. 60/125,490, filed on Mar. 22, 1999.

(51) Int. Cl.[7] .......................... C12P 21/06; C12N 15/09; C12N 9/00; C12N 1/20; C12N 5/00
(52) U.S. Cl. .................. 435/193; 435/69.1; 435/183; 435/252.3; 435/254.1; 435/254.11; 435/320.1; 435/410; 435/419; 536/23.2; 536/23.6; 536/23.7; 536/23.74
(58) Field of Search .................. 435/193, 252.3, 435/419, 6, 69.1, 183, 254.1, 254.11, 320.1, 410, 23.1; 536/23.2, 23.6, 23.7, 23.74; 800/295, 298

(56) References Cited

PUBLICATIONS

Gebler, et al., 114 *J. of the American Chemical Society* 7354 (1992).
Tsai, et al., 216 *Biochem & Biophys Res Comm* 119 (1995).
Tudzynski, et al., 261 *Molec Gen Genet* 133 (1999).
Gebler et al., 296 *Archives of Biochemistry and Biophysics* 308 (1992).
Tudzynski, et al., 103 *Mycological Research* 1044 (1999).
Arntz et al. (1997), Current Genetics, vol. 31(4):357–360, 1997.*

* cited by examiner

*Primary Examiner*—Rebecca E. Prouty
*Assistant Examiner*—Manjunath N. Rao
(74) *Attorney, Agent, or Firm*—McDermott, Will & Emery

(57) ABSTRACT

The present invention provides, inter alia, dmaW nucleic acid sequences and the proteins for which they encode. Also provided are methods for the utilization of knockout mutants of the sequences which are useful for engineering ergot alkaloid-deficient fungal symbionts (endophytes) of plants. Other methods and materials related to these sequences are also provided.

19 Claims, 4 Drawing Sheets

Figure 4

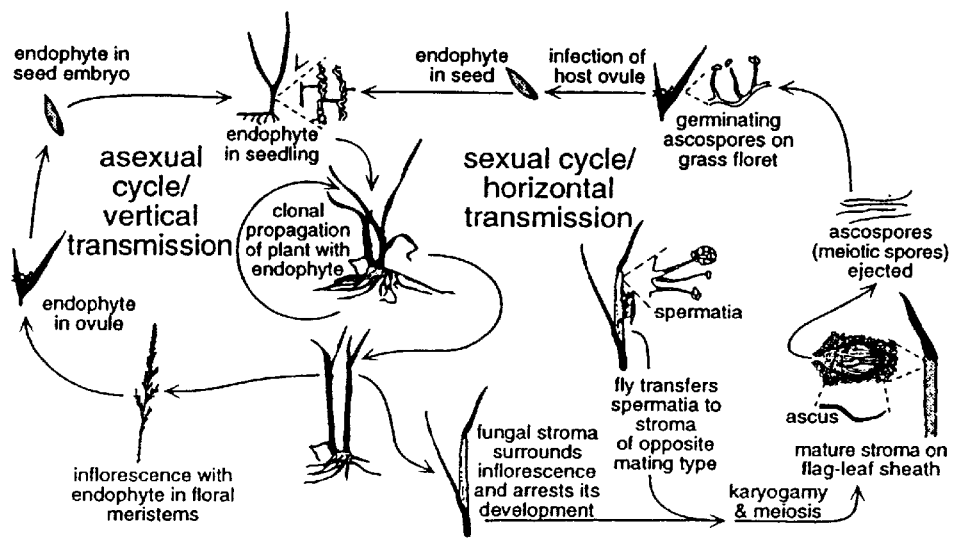

Alternative life cycles of *Epichloe* and *Neotyphodium* species in host grasses. The *Neotyphodium* (formerly *Acremonium*) endophytes have only the asexual/vertical transmission life cycle. Thus, unlike *Epichloe* species, the *Neotyphodium* species cannot transmit contagiously; that is, they cannot transmit from an infected plant of one maternal lineage to an uninfected plant of a different maternal lineage. However, the *Neotyphodium* species and some *Epichloe* species transmit vertically at extremely high frequency, such that 98%-100% of seeds produced on an endophyte-containing mother plant also contain endophyte and, upon germination, give rise to endophyte-containing plants. Also, there are standard methods whereby seedlings or other plant material that lacks endophyte can be inoculated with mycelium of wild type or transformed endophyte to give rise to endophyte-containing plants; and such plants will pass on the endophyte in the normal fashions shown here depending on whether the endophyte is compatible with that host grass and what is (are) its normal transmission mode(s) [Latch *et al.*, 107 Annals of Applied Biology 17 (1985)][Tsai *et al.*, 22 Current Genet 399 (1992)].

ly significant grasses.

SEQUENCE LISTING

<160> NUMBER OF SEQ ID NOS: 6

<210> SEQ ID NO 1
<211> LENGTH: 1347
<212> TYPE: DNA
<213> ORGANISM: Neotyphodium coenophialum

<400> SEQUENCE: 1
atggtaatgg caaagacact ccaccaggaa gtttatcata cccttagcga aacatttgac 60
tttgccaaca atgaccagag gctatggtgg cacagcacgg cgccaatgtt cgaaaagatg 120
ctccaaactg ctaactatag cattgatgct cagtatcgac atctgggcat ttataagagc 180
catgtcattc cttttcttgg tgtctatcct acaagaagtg gcgagcggtg gctaagcatt 240
cttacgagat acggaacccc gtttgagcta agtcttaatt gctcggactc cgtagttcgg 300
tatacatacg agcctattaa cgccgcaact ggcagtcatc tggatccgtt taacactttc 360
gctatctggg aggccctgaa aaagcatatt gagtcccagc caggcataga ccttgaatgg 420
ttttcttact ttaaacaaga gcttacactt gacgcaaacg agtccacgta cctgcactcg 480
caaaacttgg ttaaggaaca gatcaaaact caaaacaagc tcgctttgga ccttaaaggt 540
gacaagttcg tactgaagac ctacatctac cccgaattga agtccgtcgc aactggtaaa 600
tcggtccagg agctcgtgtt tggctccgtc cgcaagctag cgcagaagca caagagtatc 660
cgtcctgcct ttgaaatgct agaagactat gtccagtctc gcaataaatt ctctaccacg 720
gatgacagtc acaatactct attatcttca cgccttctct cttgcgacct gataagtcct 780
accaagtctc gtgtcaagat ctacctcctg gaacgaatgg tctcgttgcc agcgatggaa 840
gatctttgga cgcttggcgg ccgtcgagaa gatcagtcca ctattgaggg attggagatg 900

-continued

```
atccgagaac tttggggtct cctcaacatg tctcctggtt tgcgcgccta ccctgagcct      960
tacttgcccc tcggcgccat tcccaatgag caacttccgt ccatggccaa ttacacctta     1020
caccataatg atcccatacc agaaccgcaa gtgtacttta ctgtgttcgg catgaatgat     1080
atggaggtga ctaatgcact cacgacattc ttcatgaggc atgaatggag cgatatggca     1140
agtaaataca aagcctgcct cagggaatct ttcccgcatc atgattacga agccctgaat     1200
tatatccact cgtacatttc cttctcctac cgaaagaaca agccatattt aagtgtgtat     1260
ctccactcct ttgaaactgg taaatggcca gtgtttcccg aaggtctaat agcatttgac     1320
gcatgccggc gagatttaac ttgttaa                                         1347
```

<210> SEQ ID NO 2
<211> LENGTH: 448
<212> TYPE: PRT
<213> ORGANISM: Neotyphodium coenophialum

<400> SEQUENCE: 2

```
Met Val Met Ala Lys Thr Leu His Gln Glu Val Tyr His Thr Leu Ser
  1               5                  10                  15

Glu Thr Phe Asp Phe Ala Asn Asn Asp Gln Arg Leu Trp Trp His Ser
             20                  25                  30

Thr Ala Pro Met Phe Glu Lys Met Leu Gln Thr Ala Asn Tyr Ser Ile
         35                  40                  45

Asp Ala Gln Tyr Arg His Leu Gly Ile Tyr Lys Ser His Val Ile Pro
     50                  55                  60

Phe Leu Gly Val Tyr Pro Thr Arg Ser Gly Glu Arg Trp Leu Ser Ile
 65                  70                  75                  80

Leu Thr Arg Tyr Gly Thr Pro Phe Glu Leu Ser Leu Asn Cys Ser Asp
                 85                  90                  95

Ser Val Val Arg Tyr Thr Tyr Glu Pro Ile Asn Ala Ala Thr Gly Ser
            100                 105                 110

His Leu Asp Pro Phe Asn Thr Phe Ala Ile Trp Glu Ala Leu Lys Lys
        115                 120                 125

His Ile Glu Ser Gln Pro Gly Ile Asp Leu Glu Trp Phe Ser Tyr Phe
    130                 135                 140

Lys Gln Glu Leu Thr Leu Asp Ala Asn Glu Ser Thr Tyr Leu His Ser
145                 150                 155                 160

Gln Asn Leu Val Lys Glu Gln Ile Lys Thr Gln Asn Lys Leu Ala Leu
                165                 170                 175

Asp Leu Lys Gly Asp Lys Phe Val Leu Lys Thr Tyr Ile Tyr Pro Glu
            180                 185                 190

Leu Lys Ser Val Ala Thr Gly Lys Ser Val Gln Glu Leu Val Phe Gly
        195                 200                 205

Ser Val Arg Lys Leu Ala Gln Lys His Lys Ser Ile Arg Pro Ala Phe
    210                 215                 220

Glu Met Leu Glu Asp Tyr Val Gln Ser Arg Asn Lys Phe Ser Thr Thr
225                 230                 235                 240

Asp Asp Ser His Asn Thr Leu Leu Ser Arg Leu Leu Ser Cys Asp
                245                 250                 255

Leu Ile Ser Pro Thr Lys Ser Arg Val Lys Ile Tyr Leu Leu Glu Arg
            260                 265                 270

Met Val Ser Leu Pro Ala Met Glu Asp Leu Trp Thr Leu Gly Gly Arg
        275                 280                 285

Arg Glu Asp Gln Ser Thr Ile Glu Gly Leu Glu Met Ile Arg Glu Leu
```

```
                 290                 295                 300
Trp Gly Leu Leu Asn Met Ser Pro Gly Leu Arg Ala Tyr Pro Glu Pro
305                 310                 315                 320

Tyr Leu Pro Leu Gly Ala Ile Pro Asn Glu Gln Leu Pro Ser Met Ala
                325                 330                 335

Asn Tyr Thr Leu His His Asn Asp Pro Ile Pro Glu Pro Gln Val Tyr
            340                 345                 350

Phe Thr Val Phe Gly Met Asn Asp Met Glu Val Thr Asn Ala Leu Thr
            355                 360                 365

Thr Phe Phe Met Arg His Glu Trp Ser Asp Met Ala Ser Lys Tyr Lys
            370                 375                 380

Ala Cys Leu Arg Glu Ser Phe Pro His His Asp Tyr Glu Ala Leu Asn
385                 390                 395                 400

Tyr Ile His Ser Tyr Ile Ser Phe Ser Tyr Arg Lys Asn Lys Pro Tyr
                405                 410                 415

Leu Ser Val Tyr Leu His Ser Phe Glu Thr Gly Lys Trp Pro Val Phe
                420                 425                 430

Pro Glu Gly Leu Ile Ala Phe Asp Ala Cys Arg Arg Asp Leu Thr Cys
            435                 440                 445

<210> SEQ ID NO 3
<211> LENGTH: 1353
<212> TYPE: DNA
<213> ORGANISM: Neotyphodium coenophialum

<400> SEQUENCE: 3
atggtattgg caaagacact ccaccaggaa gtttatcaaa ccctcagcga aacatttgac      60
tttgccaaca atgaccagag gctatggtgg cacagcacgg cgccaatgtt ccaaaagata    120
ctccaaactg ctaactatag catttatgct cagtatcaac atctgagcat ttataaaagc    180
catatcattc cttttcttgg tgtctatcct acaagaagtg gcgagcggtg gctaagcatt    240
cttacgagat acggaacccc gtttgagcta agtcttaatt gctctgactc catagttcgg    300
tatacatacg agcctattaa cgccgcaact ggcagccatc tggatccgtt caacactttc    360
gctatctggg aggctctaaa aaagcttata gattcccagc caggcataga ccttcaatgg    420
ttttcctact ttaaacaaga gcttacactt gacgcaaacg agtccacgta cctgcactct    480
caaaacttgg tcaaggaaca gatcaaaact caaaacaagc tagcgttaga ccttaaaggt    540
gacaagttcg tactcaagac ctacatctac cccgaattga agtccgtcgc aactggtaaa    600
tcggtccagg agcttgtgtt tggctccgtc cgcaagctag cgcagaagca taagagtatc    660
cgtcctgcct ttgaaatgct agaagactat gtccagtctc gcaataaagt ccctaccacg    720
gatgacagtc acaatactcc attatcttca cgccttctct cttgcgacct ggtgagtcct    780
accaagtctc gtgtcaagat ctacctcctg aacgaatgg tctcgttgcc agcgatggaa    840
gatctttgga cgcttggcgg ccgtcgagaa gatcagtcca ctattgaggg attggagatg    900
atccgagaac tttggggtct ccttaacatg tctcctggtt tgcgcgccta ccctgagcct    960
tacttgcccc tcggcgccat tcccaatgag caacttccgt ccatggccaa ttacaccta   1020 caccataatg atccgatacc agaaccgcaa gtgtacttta ctgtgttcgg catgaatgat   1080
atggaggtga ctaatgcact cacgaaattc ttcatgaggc atgaatggag cgatatggca   1140
agtaaataca agcctgcct agggaatct tcccgcatc ataattacga agccctaaat    1200
tatatccact cgtacatttc cttctcctac cgaaataaca agccatattt aagtgtgtat   1260
```

```
ctccactcat ttgaaactgg tgaatggcct gtgttccccg aaggtctaat agcttttgac   1320
ggatgccggc gagatttaac ttgttataag tag                               1353
```

<210> SEQ ID NO 4
<211> LENGTH: 450
<212> TYPE: PRT
<213> ORGANISM: Neotyphodium coenophialum

<400> SEQUENCE: 4

```
Met Val Leu Ala Lys Thr Leu His Gln Glu Val Tyr Gln Thr Leu Ser
  1               5                  10                  15

Glu Thr Phe Asp Phe Ala Asn Asn Asp Gln Arg Leu Trp Trp His Ser
                 20                  25                  30

Thr Ala Pro Met Phe Gln Lys Ile Leu Gln Thr Ala Asn Tyr Ser Ile
             35                  40                  45

Tyr Ala Gln Tyr Gln His Leu Ser Ile Tyr Lys Ser His Ile Ile Pro
         50                  55                  60

Phe Leu Gly Val Tyr Pro Thr Arg Ser Gly Glu Arg Trp Leu Ser Ile
 65                  70                  75                  80

Leu Thr Arg Tyr Gly Thr Pro Phe Glu Leu Ser Leu Asn Cys Ser Asp
                 85                  90                  95

Ser Ile Val Arg Tyr Thr Tyr Glu Pro Ile Asn Ala Ala Thr Gly Ser
            100                 105                 110

His Leu Asp Pro Phe Asn Thr Phe Ala Ile Trp Glu Ala Leu Lys Lys
        115                 120                 125

Leu Ile Asp Ser Gln Pro Gly Ile Asp Leu Gln Trp Phe Ser Tyr Phe
    130                 135                 140

Lys Gln Glu Leu Thr Leu Asp Ala Asn Glu Ser Thr Tyr Leu His Ser
145                 150                 155                 160

Gln Asn Leu Val Lys Glu Gln Ile Lys Thr Gln Asn Lys Leu Ala Leu
                165                 170                 175

Asp Leu Lys Gly Asp Lys Phe Val Leu Lys Thr Tyr Ile Tyr Pro Glu
            180                 185                 190

Leu Lys Ser Val Ala Thr Gly Lys Ser Val Gln Glu Leu Val Phe Gly
        195                 200                 205

Ser Val Arg Lys Leu Ala Gln Lys His Lys Ser Ile Arg Pro Ala Phe
    210                 215                 220

Glu Met Leu Glu Asp Tyr Val Gln Ser Arg Asn Lys Val Pro Thr Thr
225                 230                 235                 240

Asp Asp Ser His Asn Thr Pro Leu Ser Ser Arg Leu Leu Ser Cys Asp
                245                 250                 255

Leu Val Ser Pro Thr Lys Ser Arg Val Lys Ile Tyr Leu Leu Glu Arg
            260                 265                 270

Met Val Ser Leu Pro Ala Met Glu Asp Leu Trp Thr Leu Gly Gly Arg
        275                 280                 285

Arg Glu Asp Gln Ser Thr Ile Glu Gly Leu Glu Met Ile Arg Glu Leu
    290                 295                 300

Trp Gly Leu Leu Asn Met Ser Pro Gly Leu Arg Ala Tyr Pro Glu Pro
305                 310                 315                 320

Tyr Leu Pro Leu Gly Ala Ile Pro Asn Glu Gln Leu Pro Ser Met Ala
                325                 330                 335

Asn Tyr Thr Leu His His Asn Asp Pro Ile Pro Glu Pro Gln Val Tyr
            340                 345                 350

Phe Thr Val Phe Gly Met Asn Asp Met Glu Val Thr Asn Ala Leu Thr
```

```
              355                 360                 365
Lys Phe Phe Met Arg His Glu Trp Ser Asp Met Ala Ser Lys Tyr Lys
    370                 375                 380

Ala Cys Leu Arg Glu Ser Phe Pro His His Asn Tyr Glu Ala Leu Asn
385                 390                 395                 400

Tyr Ile His Ser Tyr Ile Ser Phe Ser Tyr Arg Asn Asn Lys Pro Tyr
                405                 410                 415

Leu Ser Val Tyr Leu His Ser Phe Glu Thr Gly Glu Trp Pro Val Phe
                420                 425                 430

Pro Glu Gly Leu Ile Ala Phe Asp Gly Cys Arg Arg Asp Leu Thr Cys
                435                 440                 445

Tyr Lys
    450

<210> SEQ ID NO 5
<211> LENGTH: 1908
<212> TYPE: DNA
<213> ORGANISM: Neotyphodium coenophialum

<400> SEQUENCE: 5
gcattgctac ttcgctaaga agtttctttt taagttgtgt agggatttat tggatgaaac    60
cttagctagt tggctaataa tcttggaggc taggcagcaa aaccctgatt cttactatgc   120
tacatgtata atagacttcc tcagatatta atttcaaacc atgtttgcct gttagttctc   180
tctagcgcaa aggtgacttg ttagaccaca atttgttcaa tctttaactg tatcaaagaa   240
acagacaggg ctattacgct cgtcctcttc ttcacaatgg taatggcaaa gacactccac   300
caggaagttt atcataccct tagcgaaaca tttgactttg ccaacaatga ccagaggcta   360
tggtggcaca gcacggcgcc aatgttcgaa aagatgctcc aaactgctaa ctatagcatt   420
gatgctcagt atcgacatct gggcatttat aagagccatg tcattccttt tcttggtgtc   480
tatcctacaa gaagtggcga gcggtggcta agcattctta cgagatacgg aaccccgttt   540
gagctaagtc ttaattgctc ggactccgta gttcggtata catacgagcc tattaacgcc   600
gcaactggca gtcatctgga tccgtttaac actttcgcta tctgggaggc cctgaaaaag   660
catattgagt cccagccagg catagacctt gaatggtttt cttactttaa acaagagctt   720
acacttgacg caaacgagtc cacgtacctg cactcgcaaa acttggttaa ggaacagatc   780
aaaactcaaa acaagctcgc tttggacctt aaaggtgaca agttcgtact gaagacctac   840
atctaccccg aattgaagtc cgtcgcaact ggtaaatcgg tccaggagct cgtgtttggc   900
tccgtccgca agctagcgca gaagcacaag agtatccgtc ctgcctttga atgctagaa    960 gactatgtcc agtctcgcaa taaattctct accacggatg acagtcacaa tactctatta  1020
tcttcacgcc ttctctcttg cgacctgata agtcctacca agtctcgtgt caagatctac  1080
ctcctggaac gaatggtctc gttgccagcg atggaagatc tttggacgct tggcggccgt  1140
cgagaagatc agtccactat tgagggattg gagatgatcc gagaactttg gggtctcctc  1200
aacatgtctc ctggtttgcg cgcctaccct gagccttact tgcccctcgg cgccattccc  1260
aatgagcaac ttccgtccat ggccaattac accttacacc ataatgatcc cataccagaa  1320
ccgcaagtgt actttactgt gttcggcatg aatgatatgg aggtgactaa tgcactcacg  1380
acattcttca tgaggcatga atggagcgat atggcaagta aatacaaagc ctgcctcagg  1440
gaatctttgt aagtgatatc ccagctctca cattgcatga caagagttac taacataaaa  1500
atcgcttggc agcccgcatc atgattacga agccctgaat tatatccact cgtacatttc  1560
```

```
cttctcctac cgaaagaaca agccatattt aagtgtgtat ctccactcct ttgaaactgg      1620
taaatggcca gtgtgtaagt tttccaatga taatgacaat gcaatgcgcg aagggagtgg      1680
gcttctaata ctattgacta tagttcccga aggtctaata gcatttgacg catgccggcg      1740
agatttaact tgttaagtag atctgctatg gcaataagta acctttatgc acagtacgtg      1800
taatgcagat tatgaaaaga ggagacatgt aaatgcagca acaaccctag taaccaaaca      1860
aaactagtaa cgaaacaaaa tgctacgatc tttagtttgt gtttaaaa                   1908

<210> SEQ ID NO 6
<211> LENGTH: 1598
<212> TYPE: DNA
<213> ORGANISM: Neotyphodium coenophialum

<400> SEQUENCE: 6
attccgctcg tcctcttctt cacaatggta ttggcaaaga cactccacca ggaagtttat        60
caaaccctca gcgaaacatt tgactttgcc aacaatgacc agaggctatg gtggcacagc       120
acggcgccaa tgttccaaaa gatactccaa actgctaact atagcattta tgctcagtat       180
caacatctga gcatttataa aagccatatc attccttttc ttggtgtcta tcctacaaga       240
agtggcgagc ggtggctaag cattcttacg agatacggaa ccccgtttga gctaagtctt       300
aattgctctg actccatagt tcggtataca tacgagccta ttaacgccgc aactggcagc       360
catctggatc cgttcaacac tttcgctatc tgggaggctc taaaaaagct tatagattcc       420
cagccaggca tagccttca atggttttcc tactttaaac aagagcttac acttgacgca       480
aacgagtcca cgtacctgca ctctcaaaac ttggtcaagg aacagatcaa aactcaaaac       540
aagctagcgt tagaccttaa aggtgacaag ttcgtactca agacctacat ctaccccgaa       600
ttgaagtccg tcgcaactgg taaatcggtc caggagcttg tgtttggctc cgtccgcaag       660
ctagcgcaga agcataagag tatccgtcct gcctttgaaa tgctagaaga ctatgtccag       720
tctcgcaata aagtccctac cacggatgac agtcacaata ctccattatc ttcacgcctt       780
ctctcttgcg acctggtgag tcctaccaag tctcgtgtca agatctacct cctggaacga       840
atggtctcgt tgccagcgat ggaagatctt tggacgcttg gcggccgtcg agaagatcag       900
tccactattg agggattgga gatgatccga gaactttggg gtctccttaa catgtctcct       960
ggtttgcgcg cctaccctga gccttacttg cccctcggcg ccattcccaa tgagcaactt      1020
ccgtccatgg ccaattacac cttacaccat aatgatccga taccagaacc gcaagtgtac      1080
tttactgtgt tcggcatgaa tgatatggag gtgactaatg cactcacgaa attcttcatg      1140
aggcatgaat ggagcgatat ggcaagtaaa tacaaagcct gccttaggga tctttgtag       1200 gtgatatcct agttctcaca ttgcatgaca agaattacta acatataaaa atcgcttggc      1260
agcccgcatc ataattacga agccctaaat tatatccact cgtacatttc cttctcctac      1320
cgaaataaca agccatattt aagtgtgtat ctccactcat ttgaaactgg tgaatggcct      1380
gtgtgtaagt ttccaatgat aatgacaatg caatgcgcga agggaatggg cttctaatac      1440
tattaattgt agttcccgaa ggtctaatag cttttgacgg atgccggcga gatttaactt      1500
gttataagta gatctggcta tggcaataag taaccctcat gcacagtacg tgtaaggcag      1560
attatgaaga gagaagacag ttagttgcag caataacc                              1598
```

ENDOPHYTE ERGOT ALKALOID SYNTHETIC COMPOUNDS, COMPOUNDS WHICH ENCODE THEREFOR AND RELATED METHODS This application claims priority to U.S. Provisional Patent Application Serial No. 60/125,490, which was filed on Mar. 22, 1999.

The present invention was funded in part by USDA NRI grant 95-37303-1678; the U.S. Government may have certain rights in this invention.

FIELD OF THE INVENTION

The present invention relates to sequences that encode dimethylallyl-diphosphate:L-tryptophan dimethylallyltransferase ("DmaW" or "dimethylallyltryptophan synthase"), an enzyme present in some grass endophytes, and that catalyzes the formation of 4- γ,γ-dimethylallyltryptophan. This enzyme activity is the first committed step in the production of ergot alkaloids, including those with clavine and ergoline-ring structures. Such alkaloids include clavines, lysergic acid, lysergic acid amides, and ergopeptines. The sequences encode a DmaW from fungi that are symbionts of commercially significant grasses.

BACKGROUND OF THE INVENTION

Certain fungal species exist as symbiotic and integral parts of grasses and are passed from generation to generation of plants, but many are not passed from plant to plant except by transmitting in seeds of maternal plant lineages. Representatives of these fungi are the *Neotyphodium* species ("*Neotyphodium*" and sometimes "*Acremonium*", for example, *N. coenophialum*) and *Epichloe* species (e.g. *E. festucae* and *E. typhina*), which are symbionts and integral parts of many grass cultivars. These fungi, termed "endophytes", are seed-transmissible at extremely high efficiency. Their symbioses with host grasses are characterized by mutual benefits to the hosts and symbionts. Benefits to the grass hosts include protection from insects and vertebrates, and resistance to water stress (drought). Anti-insect activities are mainly due to pyrrolopyrazine and pyrrolizidine alkaloids produced by the endophytes. Anti-vertebrate activities are mainly due to indole alkaloids, including the ergot alkaloids (clavines, lysergic acid and its derivatives, and ergopeptines).

Tall fescue is grown on over 14 million hectares as an important forage, turf and conservation grass; most of the tall fescue grown in the U.S. contains ergot-alkaloid-producing endophytes. The anti vertebrate activity of the ergot alkaloids, which manifests as "tall fescue toxicosis" in cattle and other livestock, causes losses estimated at more than $600 million per year.

In 1992, Gebler and Poulter purified the DmaW enzyme from Claviceps sp. ATCC 26245 to a single protein band observable by SDS-PAGE electrophoresis, and fragmented the protein with CNBr. Gebler et al., 114 *Journal of the American Chemical Society* 7354 (1992). The three resulting fragments were purified and their N-termini sequenced. In research by one of the inventors of the present invention, there was disclosed a sequence of a dmaW gene (herein dmaW) from *C. fusiformis* ATCC 26245 organism from which the sequence was identified was mis-named *C. purpurea* by the supplier to the ATCC, and was actually *C. fusiformis*.) Tsai et al., 216 *Biochem & Biophys Res Comm* 119 (1995). The *C. fusiformis* sequence from that research is 58% identical to the present sequences at the DNA level.

More recently, a *C. purpurea* dmaW sequence was disclosed in Tudzynski et al., 261 *Molec Gen Genet* 133 (1999), and is 62% identical at the DNA level to the present sequence.

Citation of the above documents is not intended as an admission that any of the foregoing is pertinent prior art. For example, in some instances above, the publication was less than one year before the filing date of this patent application. All statements as to the date or representation as to the contents of these documents is based on subjective characterization of information available to the applicant at the time of filing, and does not constitute an admission as to the accuracy of the dates or contents of these documents.

SUMMARY OF THE INVENTION

It is therefore an object of the present invention to provide sequences useful to engineer ergot alkaloid-deficient symbionts, thus ergot-alkaloid-deficient plants.

It is a further object to provide methods to engineer ergot alkaloid-deficient endophytes.

It is yet another object to provide ergot alkaloid-deficient seeds.

It is yet another object to provide plants with ergot alkaloid-deficient endophytes.

It is also an object of the invention to provide materials such as vectors for engineering ergot alkaloid-deficient endophytes.

It is also an object of the invention to provide enzymes useful in ergot alkaloid synthesis.

Also, it is an object to use the present nucleic acid compounds to determine the potential or lack of potential of symbiont strains to produce ergot alkaloids.

Other objects will be apparent from the present disclosure.

Definitions:

For the purposes of the present application, the following terms have the following meanings. All other terms have the meaning as specifically recognized in the art.

"Allelic variant" is meant to refer to a full length gene or partial sequence of a full length gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

"Fragment" is meant to refer to any subset of the referent nucleic acid sequence.

"Knockout construct" means a DNA sequence which has been altered via any known means, for example, deletion, insertion, point mutation or rearrangement, so as to alter or eliminate the function of the naturally-occurring sequence product, but not so as to alter the ability of the DNA sequence to recombine with the naturally-occurring sequence.

"Knockout mutants" are cells, embryos, fungi or plants in which a naturally-occurring dmaW sequence has been replaced through genetic engineering with a knockout construct, so as to result in a ergot alkaloid-deficient phenotype, especially a dimethylallyl-diphosphate:L-tryptophan dimethylallyltransferase- deficient phenotype.

"Proteins" means any compounds which comprise amino acids, including peptides, polypeptides, fusion proteins, etc.

Moreover, for the purposes of the present invention, the term "a" or "an" entity refers to one or more of that entity;

for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

BRIEF DESCRIPTION OF THE DRAWINGS

FIG. 4 schematically depicts the alternative life cycles of Epichloe and Neotyphodium species in host grasses.

DETAILED DESCRIPTION OF THE INVENTION

Figure 1:
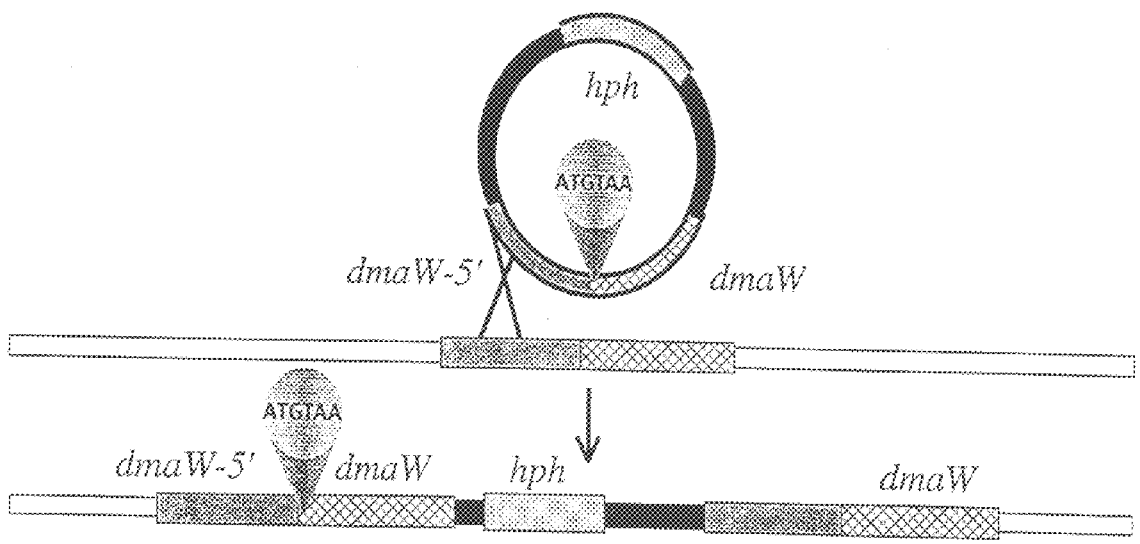
FIG. 1 schematically depicts the first step of the herein-described indirect gene replacement.

The present invention provides, inter alia, isolated nucleic acid molecule encoding a DmaW sequence, wherein said nucleic acid molecule comprises a nucleic acid sequence selected from the group consisting of:

(a) a nucleic acid sequence which has more than 63% identity to a sequence selected from the group consisting of SEQ ID NO 1 and SEQ ID NO 3, and wherein said identity can be determined using the DNAsis computer program and default parameters;

(b) a nucleic acid molecule selected from the group consisting of: a nucleic acid molecule which encodes a DmaW amino acid sequence selected from the group consisting of: SEQ ID NO 2; SEQ ID NO 4; a protein encoded by an allelic variant of SEQ ID NO 1; and a protein encoded by an allelic variant of SEQ ID NO 3.

Allelic variants, fragments (including a portion of a molecule) and homologues are, by definition of "nucleic acid molecule", included within this and other embodiments.

Included within the scope of the present invention, with particular regard to the nucleic acids above, are allelic variants, degenerate sequences and homologues. Allelic variants are expected to be found in nature. The present invention also includes variants due to laboratory manipulation, such as, but not limited to, variants produced during polymerase chain reaction amplification or site-directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid molecules (or allelic variants or degenerates thereof) can have approximately 85%, preferably approximately 90%, and most preferably approximately 95% sequence identity with a nucleic acid molecule in the sequence listing.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

In one embodiment of the present invention, a preferred dmaW nucleic acid molecule includes an isolated nucleic acid molecule which is at least about 50 nucleotides, or at least about 150 nucleotides, and which hybridizes under conditions which preferably allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO 1 and SEQ ID NO 3.

Another embodiment of the present invention includes a nucleic acid molecule comprising at least about 150 basepairs, wherein the nucleic acid molecule hybridizes, in a solution comprising 1X SSC and 0% formamide, at a temperature of about 56° C., to a nucleic acid sequence selected from the group consisting of: SEQ ID NO 1 and SEQ ID NO 3. Also preferred are fragments of any of such nucleic acid molecules.

Additional preferred dmaW nucleic acid molecules of the present invention include an isolated nucleic acid molecule which is at least about 50 nucleotides, or at least about 150 nucleotides, comprising a nucleic acid sequence that is preferably at least about 65% identical, more preferably about 70% identical, more preferably about 75% identical, more preferably about 80% identical, more preferably about 85% identical, more preferably about 90% identical and even more preferably about 95% identical to a nucleic acid sequence selected from the group consisting of SEQ ID NO 1 and SEQ ID NO 3. Also preferred are fragments of any of such nucleic acid molecules. Percent identity may be determined using the Compare function by maximum matching within the program DNAsis Version 2.1 using default parameters.

Vectors which comprise the above molecules are within the scope of the present invention, as are endophytes and other fungi transformed with the above sequences as are plants having endophytes transformed with the above sequences. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.).

Preferred vectors are those which are capable of transferring the molecules disclosed herein into fungal cells. A vector which provided for either an early or late promoter in conjunction with the present sequences would be useful in certain circumstances. For instance, the following promoters would be useful in early expression of the present sequences:

glyceraldehyde-3-phosphate dehydrogenase gene promoter [Jungehülsing et al., 25 Current Genetics 101 (1994)].

trpC promoter [Yelton et al., 82 Proceedings of the National Academy of Sciences of the United States of America 834 (1985)].

beta-tubulin gene promoter [Tsai et al., 22 Current Genetics 399 (1992)].

These are fungal promoters that are known to work in endophytes or (for the glyceraldehyde-3-phosphate dehydrogenase gene promoter) the related fungus Claviceps purpurea.

In order to then constitutively express the sequences described above, the construct optionally contains, for example, a beta-tubulin promoter according to the proceedures in Tsai et al., 22 Current Genetics 399 (1992).

Moreover, the most commercially significant use of the present invention is in the construction of "knockout mutants" using the above sequences, or known sequences, for design and construction of DmaW-deficient mutants. In other words, the present invention is informative to those skilled in the art as to their usefulness in making the naturally-occurring sequence inactive. For example, the above sequences can be mutated by any means, i.e., deletion, insertion, point mutation, rearrangement, etc, so long as the mutated version or sequences nearby in replicatable DNA of the fungus (e.g. chromosome) retains the ability to recombine. The mutated version of the sequence is then introduced into cells of a preferred line via routine methods (i.e. biolistic processes, electroporation, treatment of wall-less cells with vector, Agrobacterium-mediated transformation, etc.). DmaW-deficient mutants of the preferred line would then be selected and propagated. These "knockout" mutant embryos, seeds and plants are within the scope of the present invention, as are the knockout constructs, i.e. sequences and vectors.

Figure 2:
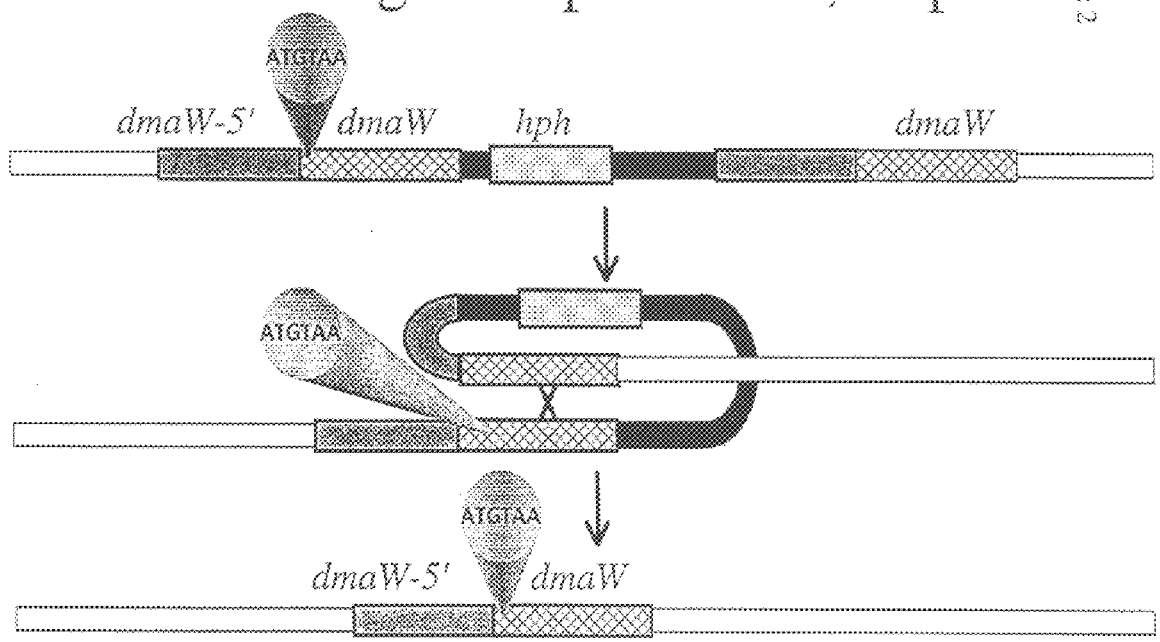
FIG. 2 schematically depicts the second step of the herein-described indirect gene replacement.
Figure 3:
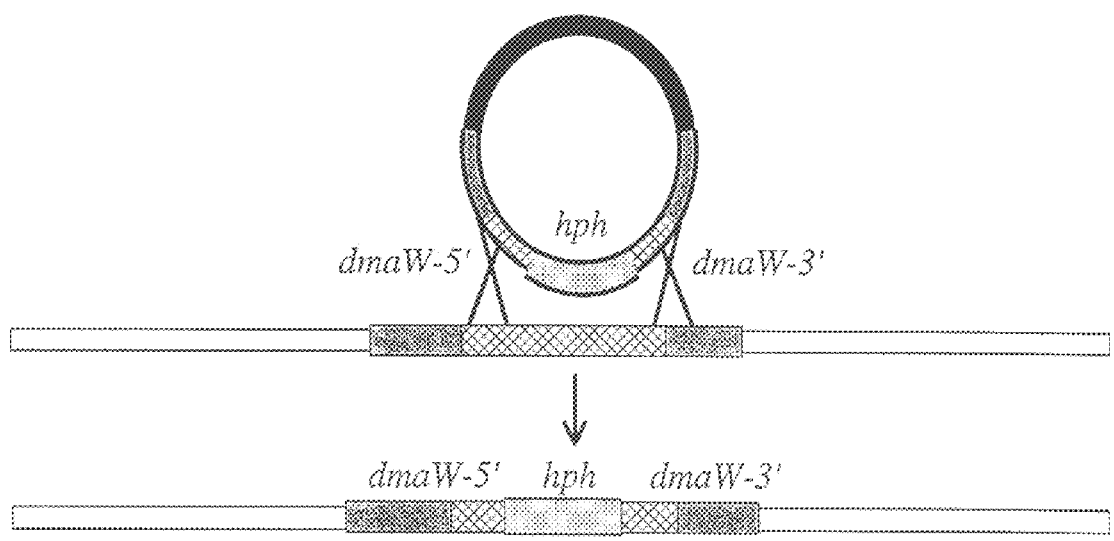
FIG. 3 schematically depicts the herein-described homologous gene replacement.

In particular, sequences near the active site of enzyme function, and the site itself, would be preferred targets. Moreover, sequences which are conserved among related organisms are also preferred targets. It is contemplated that a modification of the present invention such that the start codon has been eliminated, or replaced with a stop codon, would be a useful knockout construct. Moreover, excision of the coding region or replacing the coding region with a antibiotic (i.e. hygromycin) resistance gene would be useful. FIGS. 1 through 3 describe examples of such manipulations.

For example, the following seeds, embryos or plants with endophyte transformed with knockout constructs are considered within the present invention. Particularly preferred are: forage, turf and conservation grasses. These include, for example, tall fescue (*Festuca arundinacea*), meadow fescue (*Festuca pratensis*), and red fescue (*Festuca rubra*), which are common turf, conservation (to hold soil and reclaim strip mines) and forage grasses in the U.S. and worldwide. Also used for these purposes, are the ryegrasses such as perennial ryegrass (*Lolium perenne*). All these have endophytes and most such endophytes produce ergot alkaloids. In particular, tall fescues are most preferred. However, any seed, embryo or plant which comprise endophytes which produce ergot alkaloid is within the scope of the present invention. Of course, those in the art recognize that any seed, embryo or plant with endophyte transformed with knockout constructs which are useful for producing plants for biomass are within the scope of the present invention.

Transformation of cells with the nucleic acid molecules of the present invention can be accomplished according to known procedures. The following procedures are well known: electroporation [Tsai et al., 22 Current Genetics 399 (1992)], treatment of wall-less fungal cells with vector DNA plus CaCl2 and polyethyleneglycol [Yelton et al., 81 Proceedings of the National Academy of Sciences of the United States of America 1470 (1984)], and biolistics [Armaleo et al., 17 Current Genetics 97 (1990)]. In addition, fungi have been transformed using vector-containing bacterial strains, namely Agrobacterium tumefaciens [Gouka et al., 17 Nature Biotechnology 598 (1999)]. The transformed cells are also within the scope of this invention.

The transformed cells may be grown into a fungal mycelium (thallus), which in turn gives rise to spores. Fungal mycelium and spores are propagated indefinitely. In addition, transformed fungal endophyte can be introduced into grass plants. The current preferred method to introduce the fungus into plant is by inoculation of seedling meristems [Latch and Christensen, 107 Annals of Applied Biology 17 (1985)]. Another known method is inoculation and regeneration of plant tissue culture [Johnson et al., 70 Plant Disease 380 (1986)].

Once introduced into a plant the endophyte will remain indefinitely and propagate inside all plant propagules including tillers, stolons, and seeds (unless procedures are undertaken to eliminate live fungal mycelium in the grass, for example by long storage of seeds at ambient temperature). In any grass breeding where the female plant possesses the endophyte the seeds will almost all possess the identical endophyte, and those seeds will give rise to plants with that endophyte [Siegel et al., 74 Phytopathology 932 (1984)]. In this way a grass variety with transformed endophyte can be developed, propagated, and planted for forage, pasture, turf, revegetation, or soil conservation.

Therefore, also provided are methods for constructing sequences with the ability to knockout the above sequences, comprising one of the following techniques: inserting a foreign piece of DNA into one of the disclosed sequences; deleting a piece of DNA from one of the disclosed sequences; or creating a mutation such that the DmaW activity is eliminated.

Also provided are antisense constructs and methods to inhibit translation or accumulation of mRNA transcripts of the disclosed sequences, so as to either eliminate or reduce the amount of sequence product. The procedures for antisense inhibition for mRNA are described in U.S. Pat. No. 5,554,743, which patent is expressly incorporated by reference into this application. Alternatively, the present invention could be used to design ribozymes which specifically cleave dmaW mRNA.

Also provided in the present invention are methods to express or overexpress the dmaW sequences described herein, and using the DmaW in pharmaceutical processes. Ergot alkaloids produced in fungal fermentation or chemically modified ergot alkaloids from fungal fermentation are well known pharmaceuticals. The dmaW gene can be introduced into an ergot alkaloid-producing fungal strain, for example of C. purpurea, thus increasing the copy number and potentially the expression of the DmaW protein. Utilization of a constitutive promoter such as for beta-tubulin [Tsai et al., 22 Current Genetics 399 (1992)] may help increase expression of the gene and, thus, of the protein. Because DmaW catalyzes the rate limiting step of ergot alkaloid synthesis in C. purpurea [Lee et al., 177 Archives of Biochemistry & Biophysics 84 (1976)], its increased expression may increase ergot alkaloid production. The low level of sequence identity between dmaW from different genera (for example between dmaW sequences of Neotyphodium and Claviceps) will reduce the problem known as quenching or cosuppression which limits production of gene products in fungi and plants [Cogoni et al., 65 Antonie Van Leeuwenhoek International Journal of Microbiology 205 (1994)]. Overexpression can be as skill of the art, in particular, according to the procedures described in U.S. Pat. No. 5,477,001.

Also provided in the present invention are methods to identify Neotyphodium or Acremonium or Epichloe fungi that lack dmaW and, therefore, are unlikely to produce ergot alkaloids. The cloned Neotyphodium genes can be used for standard Southern blot hybridization, by anyone skilled in the art, to screen these related fungi for the presence of homologous genes. In addition, degenerate primers can be used for polymerase chain reaction under conditions described to amplify segments of dmaW from fungi in family Clavicipitaceae or from Neotyphodium or Acremonium species. The amplified segments can be analyzed by gel electrophoresis and sequence analysis by anyone skilled in the art. Fungi that lack DmaW can then be introduced into grass plants and thereby incorporated into breeding lines as described above.

Transformation of plant endophytes with these sequences would be according to known procedures as described above. Plants can be grown according to known procedures.

Lastly, the present sequences are useful to identify related sequences, such as those from Balansia, Balansiopsis, Echinodothis, Atkinsonella, Myriogenospora, Neotyphodium, and Parepichloe, or natural or induced mutants. For example, screening could be by Southern blot hybridization analysis of genomic DNA or by polymerase chain reaction using DNA oligonucleotide primers targeted to dmaW or the locus that contains it.

The present invention also provides isolated proteins encoded by a dmaW sequence, wherein said proteins comprise an amino acid sequence selected from the group consisting of:

(a) an amino acid sequence which has more than 68% identity to an amino acid sequence selected from the group consisting of SEQ ID NO 2 and SEQ ID NO 4 and wherein said identity can be determined using the DNAsis computer program and default parameters; and (b) an amino acid sequence which is encoded by a nucleic acid sequence of claim 1.

There are also provided recombinant cells comprising the nucleic acid molecules and/or proteins herein described.

Proteins which would result from expression of the nucleic acid molecules herein disclosed are preferred, with the proteins which would result from expression of the exemplified nucleic acid molecules being most preferred. It is understood that proteins which would result from expression of allelic variants of the exemplified sequences, as well as proteins which would result from the expression of nucleic acid molecules which hybridize under stringent hybridization conditions to the nucleic acid molecules exemplified are within the scope of the present invention as well. Lastly, an amino acid sequence substantially homologous to a referent dmaW-encoded protein will have at least 85% sequence identity, preferably 90%, and most preferably 95% sequence identity with the amino acid sequence of a referent dmaW-encoded protein or a peptide thereof. For example, an amino acid sequence is substantially homologous to dmaW-encoded protein if, when aligned with dmaW-encoded protein, at least 85% of its amino acid residues are the same. SEQ ID NO 2 and SEQ ID NO 4 are the most preferred proteins.

DmaW homologs can be the result of natural allelic variation or natural mutation. DmaW homologs of the present invention can also be produced using techniques known in the art including, but not limited to, direct modifications to the protein or modifications to the gene encoding the protein using, for example, classic or recombinant nucleic acid techniques to effect random or targeted mutagenesis.

EXAMPLE

Example 1

Obtaining dmaW sequence from *N. coenophialum*

The following degenerate primers were used to amplify genomic DNA fragments from *N. coenophialum* by polymerase chain reaction (PCR). A (+) means they correspond in sequence to a portion of mRNA, thus read 5'–3' on the gene, and a (–) indicates they are reverse complements of a portion of the mRNA and read 3'–5' on the gene: thus, each PCR involved a combination of a (+) and a (–) primer.

dmaWdeg(+)1: GAR CAR MGN YTN TGG TGG CA
dmaWdeg(+)2: GGN ATH TTY AAR AAR CAY AT
dmaWdeg(–)3: AR NGT CCA NAR RTC YTC CAT
dmaWdeg(–)4: TA NAC YTG NGG YTC NGG CAT N=A,G,C or T; Y=C or T; R=A or G; M=A or C; H=A, T or C.

Four PCR reactions were performed to amplify fragments from each fungus, using four different primer combinations, dmaWdeg(+)1 and dmaWdeg(–)3, dmaWdeg(+)1 and dmaWdeg(–)4, dmaWdeg(+)2 and dmaWdeg(–)3, dmaWdeg(+)2 and dmaWdeg(–)4. Each 50 microL reaction mixture contained 200ng fungal genomic DNA template, 200 microM each deoxyribonucleotide triphosphate (dATP, dGTP, dTTP and dCTP), 25 mM each primer, 1 X PCR buffer (Perkin-Elmer), and 2.5 units Taq DNA polymerase (AmpliTaq Gold from Perkin-Elmer). Reactions were held at 93 ° C. for 9 min and 95° C. for 3 min, then subjected to 35 cycles of the following profile: 94° C. for 45 s, 53° C. for 45 s, 72° C. for 80 s in a Perkin-Elmer model 2400 Thermal Cycler. After completing these temperature cycles the reactions were incubated 5 min at 72° C., then analyzed by agarose gel electrophoresis.

The resulting amplified genomic fragments were cloned and used as probes of a cosmid library (and thus obtained SEQ ID NO 1 of *N. coenophialum* dmaW), or the sequences were used as a basis for new primers for anchored single primer PCR (and thus obtained SEQ ID NO 3 of *N. coenophialum* dmaW).

Clones were sequenced using PE Biosystems Model 310 Genetic Analyzer. DNA sequence analysis was carried out with the DNAsis (Hitachi) and GCG (University of Wisconsin Genetics Computer Group, Madison) sequence analysis packages. Alignment of sequences was done using CLUSTAL W according to Thompson et al., 22 Nucl. Acids Res. 4673 (1994).

Example 2

Construction of knockout mutants

Clones will be constructed containing DNA of each dmaW locus from which all or part of the gene has been deleted, or in which the dmaW has been mutated to a form expected to be inactive. These clones will be used in transformation experiments as described in Tsai et al, 22 *Genetics* 399 (1992). Transformants will be screened by Southern blot hybridization and polymerase chain reaction to identify those that have had the wild type gene replaced by the mutant form. In endophytes with more than one dmaW copy, such as *N. coenophialum*, the procedure will be repeated until all active or potentially active copies are replaced with inactive forms. The endophyte, so altered, will be introduced into its natural host, and the loss of ergot alkaloid synthetic properties of the endophyte/grass symbiosis will be determined by standard chemical methods.

Example 3

Identity comparisons

The GAP program of the Wisconsin Genetics Group GCG package was used to compare the original sequence from ATCC 26245 (C. fusiformis) with SEQ ID NO 1 and SEQ ID NO 3, and likewise with the *C. purpurea* ATCC 20102 dmaW gene (sequenced by the present lab, and identical to the sequence published by Tudzynski et al, cited in Background). Comparisons both with nucleic acid and with amino acid sequences were made, though for hybridization analysis only the nucleic acid identity is of importance. In each case the SEQ ID NO 1 gave slightly higher identity. In nucleotide sequence it was 62.295% identical to the ATCC 26245 and 62.416% to the ATCC 20102 gene. In amino acid sequence its inferred protein product was 61.745% identical to that of the ATCC 26245 and 67.040% to that of the ATCC 20102 gene.

Although the present invention has been fully described herein, it is to be noted that various changes and modifications are apparent to those skilled in the art. Such changes and modifications are to be understood as included within the scope of the present invention as defined by the appended claims.

What is claimed is:

1. An isolated nucleic acid molecule, wherein said nucleic acid molecule comprises a nucleic acid sequence selected from the group consisting of:
    (a) a nucleic acid molecule encoding a dimethylallyltryptophan synthase (DmaW molecule) which has more than 70% identity to a molecule selected from the group consisting of SEQ ID NO 1 and SEQ ID NO 3, and wherein said identity can be determined using the DNAsis computer program and default parameters;
    (b) a nucleic acid molecule selected from the group consisting of: a nucleic acid molecule which encodes a DmaW amino acid molecule selected from the group consisting of: SEQ ID NO 2; and SEQ ID NO 4; and
    (c) a nucleic acid molecule fully complementary to a nucleic acid molecule selected from the group consisting of: a nucleic acid molecule of (a); and a nucleic acid molecule of (b).

2. A knockout construct of a dmaW molecule of claim 1.

3. A vector comprising a knockout construct of claim 2.

4. A fungus comprising a knockout construct of claim 2.

5. A seed comprising a fungus of claim 4.

6. An embryo comprising a fungus of claim 4.

7. A plant comprising a fungus of claim 4.

8. A plant of claim 7, which is a forage grass.

9. A plant of claim 8, which is a fescue.

10. A plant of claim 9, which is a *Festuca arundinacea*.

11. A method to express DmaW in a cell, comprising transforming a cell with a molecule of claim 1; and incubating said cell under such conditions so as to cause expression of DmaW.

12. A method to identify endophytes that contain or lack a dmaW gene, comprising contacting a nucleic acid molecule of claim 1 with DNA of a sample endophyte under 1×SSC and 0% formamide at about 56° C. hybridization wash conditions, and determining if said endophyte contains or lacks the dmaW gene based on the results of the hybridization reaction.

13. A method of claim 12, wherein said sample endophyte is used in commercial plants selected from the group consisting of forage, pasture, turf, land reclamation, and soil conservation.

14. A method for producing increased amount of ergot alkaloids, comprising expressing the nucleic acid molecule according to claim 1 in a host fungal cell, so the copy number of messenger RNA derived from transcription of said nucleic acid molecule is increased, and allowing said host fungal cell to grow under appropriate growth conditions, which causes increased production of ergot alkaloid.

15. The isolated nucleic acid molecule according to claim 1, wherein said nucleic acid molecule encoding a DmaW molecule has more than 75% identity to the nucleic acid molecule having the sequence set forth in SEQ ID NO: 1 or SEQ ID NO:3.

16. The isolated nucleic acid molecule according to claim 1, wherein said nucleic acid molecule encoding a DmaW molecule has more than 80% identity to the nucleic acid molecule having the sequence set forth in SEQ ID NO:1 or SEQ ID NO:3.

17. The isolated nucleic acid molecule according to claim 1, wherein said nucleic acid molecule encoding a DmaW molecule has more than 85% identity to the nucleic acid molecule having the sequence set forth in SEQ ID NO:1 or SEQ ID NO:3.

18. The isolated nucleic acid molecule according to claim 1, wherein said nucleic acid molecule encoding a DmaW molecule has more than 90% identity to the nucleic acid molecule having the sequence set forth in SEQ ID NO:1 or SEQ ID NO:3.

19. The isolated nucleic acid molecule according to claim 1, wherein said nucleic acid molecule encoding a DmaW molecule has more than 95% identity to the nucleic acid molecule having the sequence set forth in SEQ ID NO:1 or SEQ ID NO:3.

* * * * *